(12) United States Patent
Cabanis et al.

(10) Patent No.: US 7,768,259 B2
(45) Date of Patent: Aug. 3, 2010

(54) DEVICE FOR NON-DESTRUCTIVE EDDY CURRENT INSPECTION OF A HOLE FORMED IN A CONDUCTIVE PART

(75) Inventors: Patrick Cabanis, Les Etards Ozouer le Voulgis (FR); Sandra Carole Angele Cheynet, Le Plessis Pate (FR); Patrick Gaisnon, Cannes Ecluse (FR); Christian Le Corre, Saint Fargeau pont Thierry (FR)

(73) Assignee: SNECMA, Paris (FR)

( * ) Notice: Subject to any disclaimer, the term of this patent is extended or adjusted under 35 U.S.C. 154(b) by 101 days.

(21) Appl. No.: 12/123,029

(22) Filed: May 19, 2008

(65) Prior Publication Data

US 2008/0297148 A1    Dec. 4, 2008

(30) Foreign Application Priority Data

May 29, 2007    (FR) .................................. 07 55290

(51) Int. Cl.
*G01N 27/82* (2006.01)
*G01N 27/90* (2006.01)
(52) U.S. Cl. .................. 324/220; 324/238; 324/240
(58) Field of Classification Search ................. 324/220, 324/238, 240
See application file for complete search history.

(56) References Cited

U.S. PATENT DOCUMENTS

| | | | | |
|---|---|---|---|---|
| 5,291,136 A | * | 3/1994 | Van der Veer et al. | ....... 324/262 |
| 5,781,007 A | | 7/1998 | Partika et al. | |
| 6,894,492 B1 | * | 5/2005 | Dziech | ....................... 324/238 |

FOREIGN PATENT DOCUMENTS

| EP | 1 605 259 A1 | 12/2005 |
|---|---|---|
| FR | 2 871 568 | 12/2005 |

OTHER PUBLICATIONS

U.S. Appl. No. 12/436,829, filed May 7, 2009, Briffa, et al.
U.S. Appl. No. 12/211,357, filed Sep. 16, 2008, Briffa, et al.
U.S. Appl. No. 12/102,460, filed Apr. 14, 2008, Briffa, et al.
U.S. Appl. No. 12/104,948, filed Apr. 17, 2008, Bousquet, et al.

* cited by examiner

*Primary Examiner*—Reena Aurora
(74) *Attorney, Agent, or Firm*—Oblon, Spivak, McClelland, Maier & Neustadt, L.L.P.

(57) ABSTRACT

Using eddy currents to inspect a hole that is possibly not rectilinear and/or of section that is not circular. The inspection device comprises a stick shaped and dimensioned to be capable of being engaged in said hole, at least one arm hinged to a support fastened to one end of the stick, an eddy current sensor being embedded in said arm, and resilient means for urging the arm outwards against the inside surface of the hole.

9 Claims, 2 Drawing Sheets

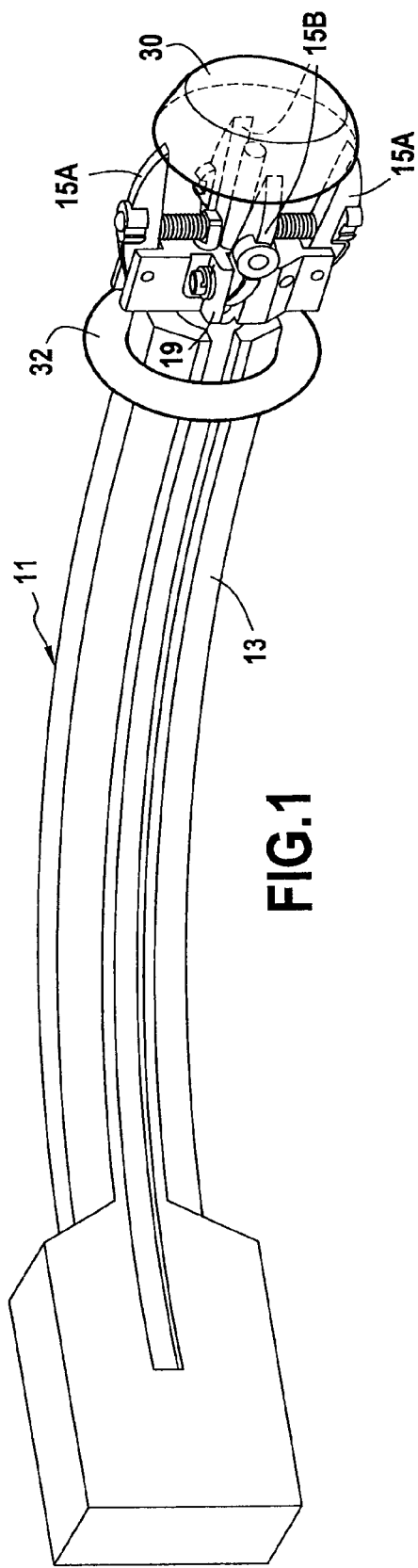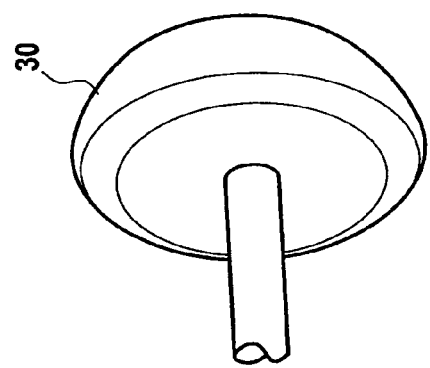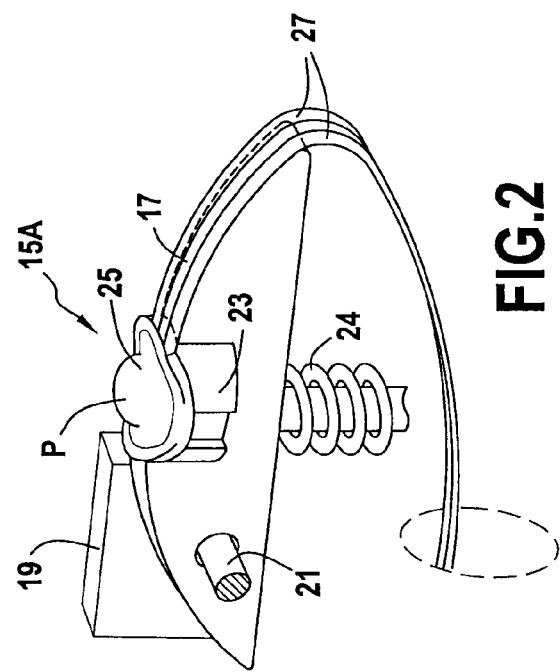

DEVICE FOR NON-DESTRUCTIVE EDDY CURRENT INSPECTION OF A HOLE FORMED IN A CONDUCTIVE PART

The invention relates to a device for non-destructive eddy current inspection of a hole formed in a conductive part, in particular a metal part, the device being more particularly adapted to explore said hole by broaching, without turning, said hole being non-rectilinear and/or of section that is non-circular. By way of non-limiting example, the invention makes it possible to inspect cooling or air bleed holes formed in a rotor disk of a turbomachine.

BACKGROUND OF THE INVENTION

In a turbojet disk, such as a high pressure turbine disk, curved holes are provided that extend between one of the faces of the disk and the bottoms of tangential cells for retaining blades. These holes serve to inject cooling air. A similar arrangement is provided on certain high pressure compressor disks for bleeding air.

In addition, these holes are generally of section that is not circular; they are usually elliptical in section. Conventionally, these holes are inspected by means of eddy currents, requiring a plurality of appropriate probes to be inserted therein and requiring broaching to be performed on each occasion in order to scan the inside surface of the hole along parallel longitudinal strips. The purpose of performing eddy current inspection is to identify any anomalies in the surface state of the hole, and in particular the formation of small cracks in the surface or underlying it. Contact between the probe and the surface of the hole needs to be maintained throughout the broaching operation in order to ensure that the inspection is reliable. Unfortunately, such holes may be of varying section, i.e. of section that is not exactly the same over their entire length, and they may also present local variations in curvature.

A known system comprises a set made up of a plurality of curved arms, each carrying a probe containing an eddy current sensor. Each probe has a split end that is resiliently flexible and that contains the sensor. That system lacks sensitivity and accuracy since the surface area that is scanned during broaching is too large, and above all because it is not certain that good contact will be obtained between the outside surface of the probe, on the best point thereof, and the inside surface of the hole.

The invention provides an improvement to a system of that type.

OBJECTS AND SUMMARY OF THE INVENTION

More particularly, the invention provides a device for non-destruction eddy current inspection of a hole formed in a conductive part, the device being of the type suitable for exploring said hole by broaching without rotation, the device comprising a stick shaped and dimensioned to be capable of being engaged in said hole, and comprising:

- at least one hinged arm in the vicinity of one end of said stick and including a curved outside face;
- an eddy current sensor embedded in said arm in the vicinity of said curved outside face; and
- resilient means for urging said hinged arm outwards, the arrangement being such that said hinged arm is in sliding contact with the inside surface of the hole.

To protect the sensor, it is advantageous to cover it in resin. Under such conditions, it is the hardened resin that comes into contact with the inside surface of the hole.

To inspect a curvilinear hole, the stick is curved, and the curvature of the stick corresponds to the curvature of the hole. Preferably, the stick carries at least two of said hinged arms, in opposition.

Preferably, such a stick carries a plurality of pairs of said hinged arms.

In an embodiment, the or each arm is hinged on a pin to a support secured to said stick, and a spring is installed between said stick and said arm, in order to push the arm outwards.

For a hole of section that is not circular, in particular a hole of elliptical section, the arms of such a pair are spaced apart at a distance that corresponds to the width of the hole between the sensors in question.

Advantageously, the device further includes a guide part having an outline that corresponds to the section of the hole. The guide part is placed at the end of the stick. It is also advantageous for a rear guide part to be fastened to the stick, behind the arm(s), the rear part having an outline that corresponds to the section of the hole. In order to inspect a hole of curvature and/or section that are predetermined, use will generally be made of a plurality of inspection devices of the above-described type. The inspection devices in a given set are similar (in particular they have similar sticks), but they differ from one another by the positions of the arms that are hinged to their ends. The sensors carried by all of the arms of the various devices are designed to be placed in register with selected respective generator lines of the hole so as to be capable of scanning the surface state of the hole in parallel narrow strips.

BRIEF DESCRIPTION OF THE DRAWINGS

The invention can be better understood and other advantages thereof appear more clearly in the light of the following description of several inspection devices implementing the invention, given purely by way of example and with reference to the accompanying drawings, in which:

FIG. 1 is an overall perspective view of an inspection device in accordance with the invention;

FIG. 1A is a rear view of a detail showing the front guide part of FIG. 1;

FIG. 2 is a detail view on a larger scale of an arm carrying a sensor, forming part of the FIG. 1 device.

MORE DETAILED DESCRIPTION

Figure 3:
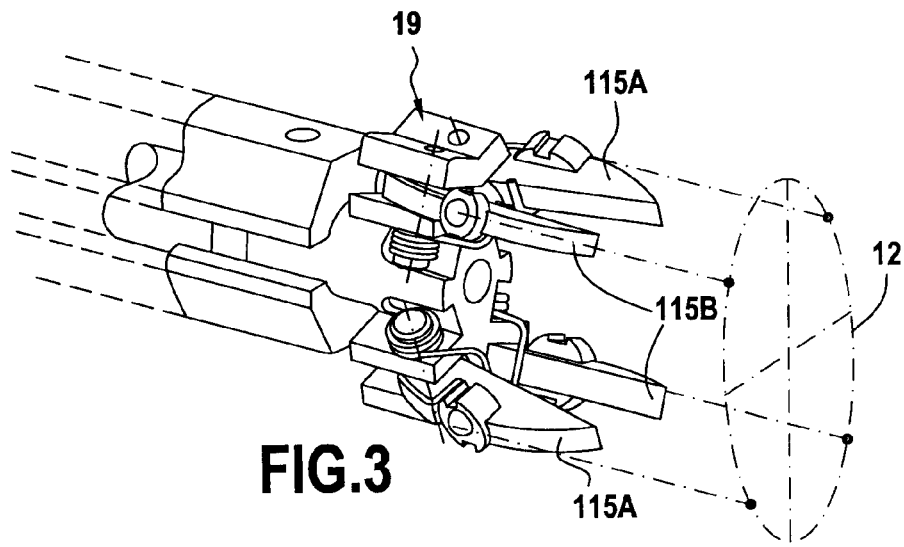
FIGS. 3 to 5 are detail views of a plurality of devices similar to that of FIG. 1, together showing a certain number of sensors positioned in different locations.

The inspection device 11 shown in FIGS. 1 and 2 is designed to scan at least a narrow strip of the inside surface of a hole 12 formed in a conductive part, in this example made of metal. In this example, the hole presents a radius of curvature that is constant and an outline that is not circular, specifically that is elliptical. This type of hole can be found in a high pressure turbine disk of a turbojet. The hole extends between one side of the disk and the bottom of a tangential cell serving to retain a blade root. Air is injected into such a hole in order to cool the blade root. The invention makes it possible to use eddy currents to inspect the surface of such a hole in non-destructive manner.

Naturally, the inspection device of the invention may be suitable for or adapted to scan the surface state of any hole formed in a conductive part by broaching (or even to scan the structure of the material in the vicinity of said surface, over a certain depth).

The device comprises a stick 13 of shape and dimensions suitable for being engaged in the hole. By way of example, the stick may be mounted at the end of an arm of a robot that is programmed to cause it to follow a suitable trajectory, e.g. along its own line of curvature. The sleeve needs to have a section that is smaller than that of the hole so as to be capable of being engaged therein without coming into contact with its inside surface. As shown, the sleeve is curved, and this curvature corresponds to the curvature of the hole. For example, if the hole is curved with a constant radius of curvature, the sleeve has a radius of curvature that is substantially equal to that of the hole.

In the vicinity of its end, the sleeve 13 carries at least one hinged arm. The arm has a curved outside face 17. Preferably, the stick carries at least two of the above-mentioned hinged arms 15A placed in opposition. More precisely, the arms are positioned so that the points of contact they make with the surface of the hole are substantially symmetrical about the center of the section of the hole. In a preferred embodiment, the stick carries a plurality of pairs of the above-mentioned hinged arms 15A, 15B. In the examples described, such a stick carries two pairs of hinged arms.

As shown in the drawing, the stick has a support 19 at its end, and each arm is mounted to pivot about a pin 21 on the support. The orientation of the pin is such that the arm 15A, 15B pivots in a plane that is substantially perpendicular to the surface for scanning and containing the point of contact between the curved outside face of the arm and said surface.

An eddy current sensor 23 is embedded in the arm close to its curved outside face 17, and more particularly in the vicinity of the intended point of contact P between said side face and the surface for inspection. Each sensor is covered by a drop of resin 25 serving to protect it. Good anti-wear performance is obtained by filling the resin with materials such as silicon carbide, alumina, or ceramic.

In addition, resilient means are provided for urging each hinged arm outwards so that the arm is in contact with the inside surface of the hole, the point of contact P being situated in the vicinity of the sensor. In the example, a spring 2.4 is mounted between the support situated at the end of the stick and the hinged arm. Depending on circumstances, and in particular on the amount of room available, the spring may be a simple helical spring acting in compression between the support and the arm, or it may be a spiral spring about a rod. Electric wires 27 connected to the sensor run along the surface of the arm and are engaged in a channel in the stick.

The device further comprises at least one guide part enabling the sensors to be positioned more accurately relative to the section of the hole. Thus, there can be seen a front guide part 30 that is placed at the end of the stick. This guide part presents an outline that matches the section of the hole, i.e. in this example it is elliptical. Its section flares from front to back, up to a section close to that of the hole.

A rear guide part 32 is also provided that is fastened to the stick between the set of pivot arms. This rear guide part also has an outline corresponding to the section of the hole. Thus, once the guide parts are engaged in the hole, each pivot arm is constrained to follow a predetermined line extending along the length of the hole, so that the corresponding sensor 23 can scan the surface state of a narrow strip on either side of said line of contact.

Figure 4:
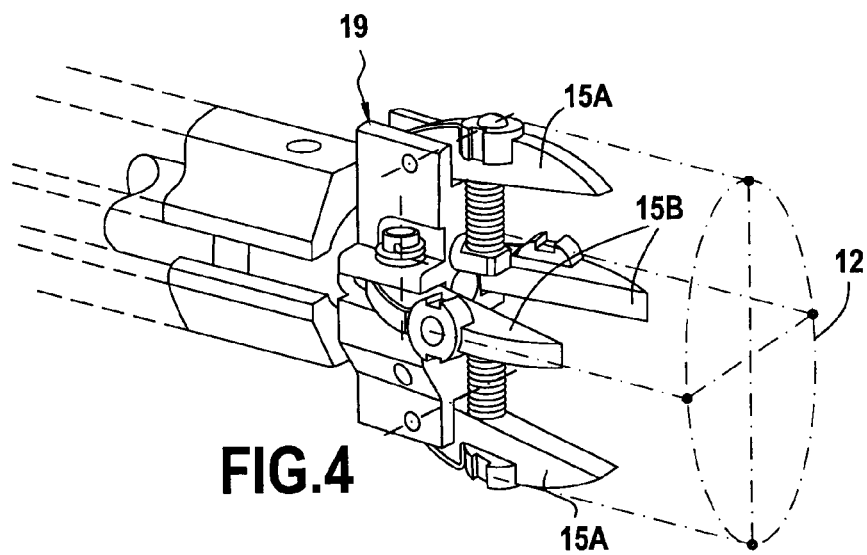
Figure 5:
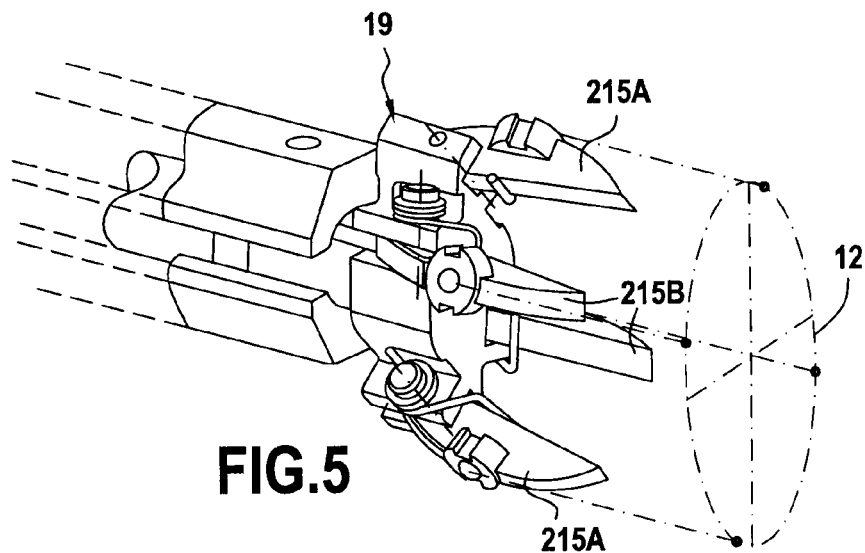

As can be seen in FIGS. 3 to 5, a complete eddy current inspection kit has a plurality of inspection devices as described above that differ from one another by the positions of the hinged arms (15A, 115A, 215A-15B, 115B, 215B) they carry, relative to the section of the hole 12. Thus, by performing as many broaching operations as there are inspection devices, it is possible to obtain a set of signals representative of the surface state of a corresponding number of parallel and adjacent strips on the inside surface of the hole. This information taken as a whole serves to obtain an accurate survey of any defects in the inside surface of the hole or a little beneath said surface.

The invention is applicable to parts made of composite material based on carbon since carbon is a conductor.

What is claimed is:

1. A device for non-destruction eddy current inspection of a hole formed in a conductive part, the device being configured to explore said hole by broaching without rotation, the device comprising a stick shaped and dimensioned to be capable of being engaged in said hole, and comprising:
   at least one hinged arm in a vicinity of one end of said stick and including a curved outside face;
   an eddy current sensor embedded in said arm in a vicinity of said curved outside face; and
   resilient means for urging said hinged arm outwards, wherein said hinged arm is in sliding contact with an inside surface of the hole, said sliding contact taking place in the vicinity of the curved outside face of said sensor.

2. A device according to claim 1, for inspecting a curvilinear hole, wherein said stick is curved, with curvature corresponding to the curvature of the hole.

3. An inspection device according to claim 1, wherein said stick carries at least two of said hinged arms, in opposition.

4. A device according to claim 3, wherein said stick carries a plurality of pairs of said hinged arms.

5. A device according to claim 1, wherein the or each arm is hinged on a pin to a support secured to said stick, and wherein a spring is installed between said stick and said arm, in order to push the arm outwards.

6. A device according to claim 1, wherein the or each sensor is covered in resin.

7. A device according to claim 1, wherein a front guide part is placed at the end of said stick, said guide part having an outline corresponding to the section of said hole.

8. A device according to claim 1, wherein a rear guide part is fastened to said stick, behind said arm(s), said rear guide part having an outline corresponding to the section of said hole.

9. A kit for performing eddy current inspection of a hole formed in a conductive part, the kit comprising a plurality of inspection devices according to claim 1, the devices differing from one another by the positions of the hinged arms they carry relative to the section of the hole.

* * * * *